United States Patent [19]

Ryder

[11] 4,251,719
[45] Feb. 17, 1981

[54] CONTACT LENS DISINFECTOR WITH TEMPERATURE INDICATOR

[75] Inventor: Francis E. Ryder, Arab, Ala.

[73] Assignee: Ryder International Corporation, Arab, Ala.

[21] Appl. No.: 51,122

[22] Filed: Jun. 22, 1979

[51] Int. Cl.³ .................... H05B 3/06; C01F 1/00; A61L 2/00
[52] U.S. Cl. .................... 219/521; 422/119; 422/300; 116/221; 40/492; 219/449
[58] Field of Search .............. 422/292, 119, 199, 300; 116/221 X; 73/363.5, 363.7; 206/305, 306; 246/169 R, 169 A; 219/438, 439, 441, 510, 512, 521, 449; 40/492

[56] References Cited

U.S. PATENT DOCUMENTS

| | | | |
|---|---|---|---|
| 1,390,987 | 9/1921 | Denison | 73/363.7 |
| 1,581,812 | 4/1926 | Ryan et al. | 116/221 |
| 2,181,303 | 11/1939 | Leingang et al. | 116/221 |
| 3,214,278 | 10/1965 | Mylo | 116/221 |
| 3,494,321 | 2/1970 | Moore et al. | 116/221 |
| 3,863,048 | 1/1975 | Buckley | 219/521 |
| 3,983,362 | 9/1976 | Hoogesteger et al. | 422/300 |
| 4,091,763 | 5/1978 | Snider | 116/221 |
| 4,141,247 | 2/1979 | Schlick | 116/221 |

Primary Examiner—William F. Smith
Assistant Examiner—Chris Konkol
Attorney, Agent, or Firm—Trexler, Wolters, Bushnell & Fosse, Ltd.

[57] ABSTRACT

A contact lens disinfector unit (10) includes a housing, heating means (20) within the housing and arranged to heat the contact lens case (21) and the contact lenses therein to a disinfecting temperature and for terminating the application of heat thereafter to allow the contact lenses to cool, and temperature indicating means (30) that includes a partially opaque viewing window (17) formed in the housing, a movable member (36) having a substantially planar surface (37) which includes temperature indicia corresponding to a "HOT" condition of the lens case, and a bi-metallic member (32) responsive to the temperature of the heating means (20) for moving the movable member planar surface toward and away from window (17) to indicate the "HOT" condition or a condition where the lens case is cool enough for handling.

4 Claims, 5 Drawing Figures

CONTACT LENS DISINFECTOR WITH TEMPERATURE INDICATOR

BACKGROUND OF THE INVENTION

The present invention relates to a contact lens disinfector unit with an improved temperature indicator.

Disinfector units of the prior art have generally controlled the application of electric current to the heating block with a thermocouple switch. The thermocouple, after detecting a predetermined temperature of the heating block, breaks the switch contact for terminating the application of the electric current. Wires in series with the switch is usually a lamp. The lamp lights up when the switch is closed and electric current is being applied to the heating block, and is turned off when the thermocouple opens the switch to terminate the application of the electric current to the heating block. Because of this arrangement, the user never knows when the contact lens case has cooled sufficiently to be safely removed from the disinfector unit. The user may therefore either attempt to remove the lens case too soon, resulting in possible injury, or wait an exceedingly long time after the lamp turns off to be assured that the lens case may be safely removed. As a result, such disinfectors are inconvenient to use and may result in injury to the user.

It is therefore an object of the present invention to provide a new and improved contact lens disinfector unit which includes an arrangement for indicating when the contact lens case is hot and unsafe for removal, and conversely for indicating when the lens case has cooled sufficiently for safe removal.

In one embodiment the invention provides a contact lens disinfector unit for disinfecting contact lenses contained within a contact lens case. The disinfector unit includes a housing, heating means within the housing and arranged to heat the contact lens case and the contact lenses therein to a disinfecting temperature and for terminating the application of heat thereafter to allow the contact lenses to cool, and temperature indicating means for indicating first and second temperatures of the heating means. The temperature indicator includes a partially opaque viewing window formed in the housing, a movable member having a substantially planar surface which includes temperature indicia correponding to one of the heating means temperatures, and actuating means responsive to the temperature of the heating means for moving the movable member planar surface against the window for rendering the indicia viewable through the window responsive to the heating means being at a first temperature, and for displacing the movable member planar surface away from the window and for removing the indicia from view through the window responsive to the means being at a second temperature.

DESCRIPTION OF THE PREFERRED EMBODIMENT

Figure 1:
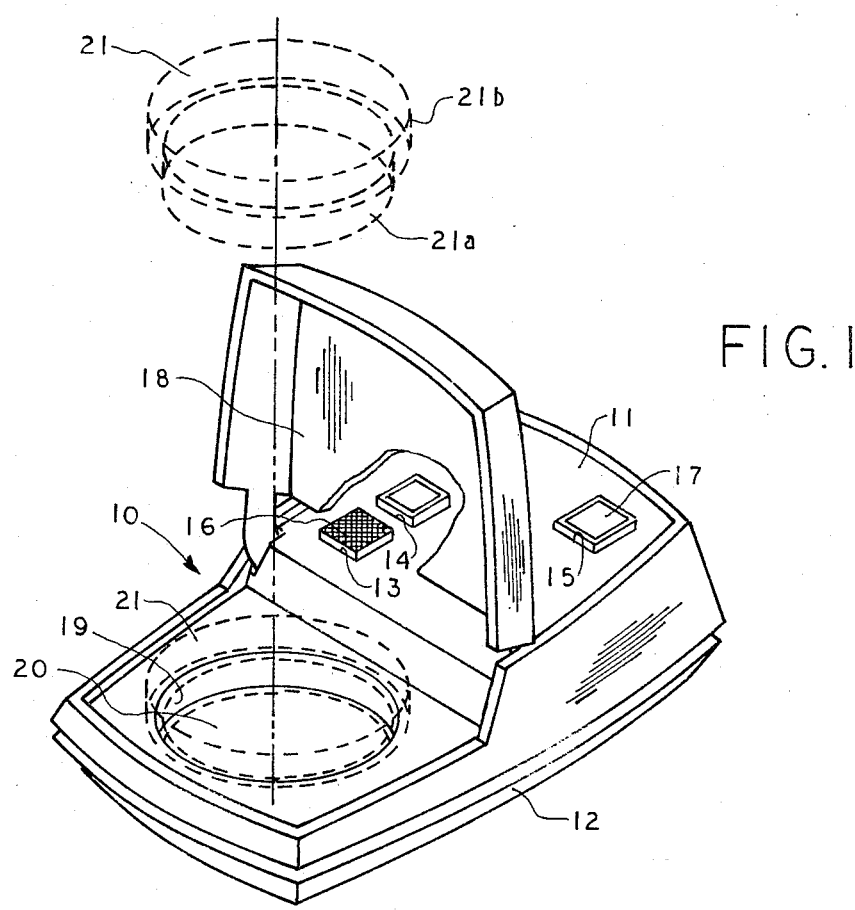
FIG. 1 is a perspective view of a contact lens disinfector unit embodying the present invention showing its hinged cover in a raised position in a contact lens case (in dashed lines) shown both in an exploded position relative to the disinfector unit and also in position in the unit.
Figure 2:
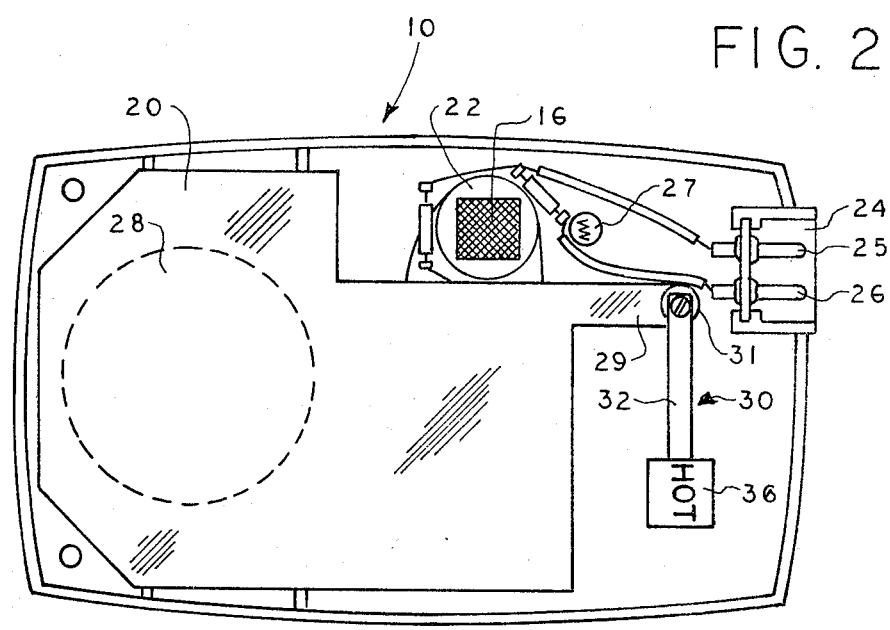
FIG. 2 is a top, plan view of the interior of the disinfector unit of FIG. 1, the top or cover portion of the unit housing having been removed.

Referring now to FIGS. 1 and 2, the disinfector unit 10 includes a housing having a top cover section 11, and a bottom section 12. The section 11 has openings 13, 14 and 15. In a first opening 13 there is an actuator button 16 mechanically coupled to a thermocouple switch 22. When button 16 is depressed, a disinfecting cycle is initiated. The second opening 14 is disposed over an internal light bulb 27 which lights up when the thermocouple switch 22 is closed, thereby indicating that the unit 10 is in the heating mode. The light bulb 27 becomes de-energized when the thermocouple switch 22 opens upon reaching a disinfecting temperature. The opening 15 receives a partially opaque (e.g. translucent) viewing window 17 of the temperature indicating means of the present invention through which the user may be informed that the contact lenses are hot and unsafe for removal, or alternatively that the contact lenses have cooled sufficiently so as to be removed from the disinfector unit. The window 17 may be of glass or plastic.

The top cover section 11 includes a hinged lid portion 18 shown in a raised or open position so that the lens case 21 may be inserted and removed from the housing. In addition, the top cover 11 includes a circular recess 19 which communicates with the upper surface of a heating block 20 disposed internally of the unit 10, and which recess 19 is dimensioned for receiving a lens case 21 shown in dashed outline. The lens case 21 may be of any of several types well known in the art, which include a bottom portion 21a removably engaged with an upper portion 21b, with one of the portions adapted to accommodate a pair of lenses and a quantity of disinfecting solution. Preferably, the lens case 21 and the recess 19 are dimensioned such that the bottom surface of the lens case makes direct surface-to-surface contact with the upper surface of the heating block 20. During the disinfecting cycle, the heating block 20 provides sufficient heat transfer to the lens case 21 so as to heat the contact lenses and the solution to a disinfecting temperature sufficient to kill pathogenic bacteria on the lenses.

The disinfector unit 10 includes the aforementioned heating block 20, the thermocouple switch 22 with its recessed button 16 that extends through the opening 13, and a power supply circuit for a conventional resistive heating element. The power supply circuit is adapted to be connected to an electric power source by pins 25 and 26 of connector 24. When the button 16 is depressed the switch 22 is closed so that current is supplied to the resistive heating element. When the correct temperature of the lens case and/or solution therein is reached, the thermocouple switch opens, shutting off the current to the resistive heating element and to the lamp 27. The heating block 20 includes a surface portion 28 shown in dashed lines which engages the under surface of the lens case 21 during the disinfection of the contact lenses. The heating block includes a rearward portion 29 which terminates in an upstanding post 31 to which the temperature indicating arrangement 30 is operatively connected. In a known manner the heating block 20 is in contact with the resistive heating element to heat the disinfecting solution. The circuit means providing power to the resistive heater is of a type well known in the art and need not be described in detail herein.

Figure 3:
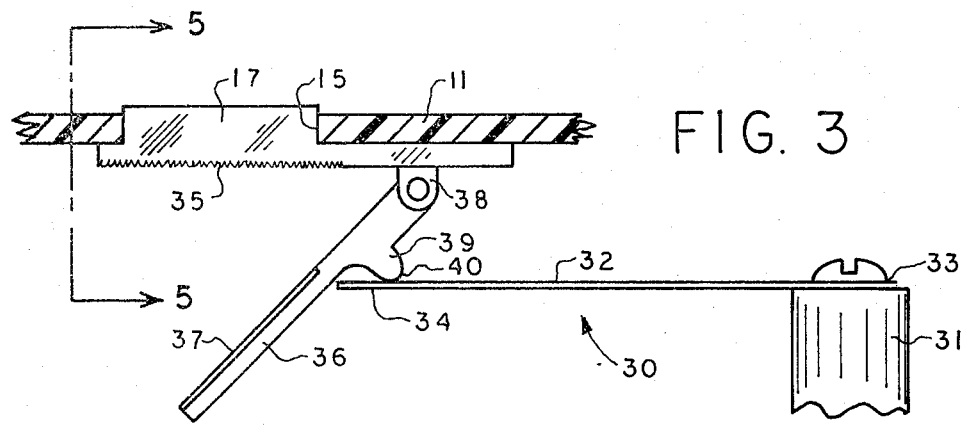
FIG. 3 is a partially cross-sectional side view of a temperature indicator embodying the present invention illustrating the temperature indicator in a first operative position.
Figure 4:
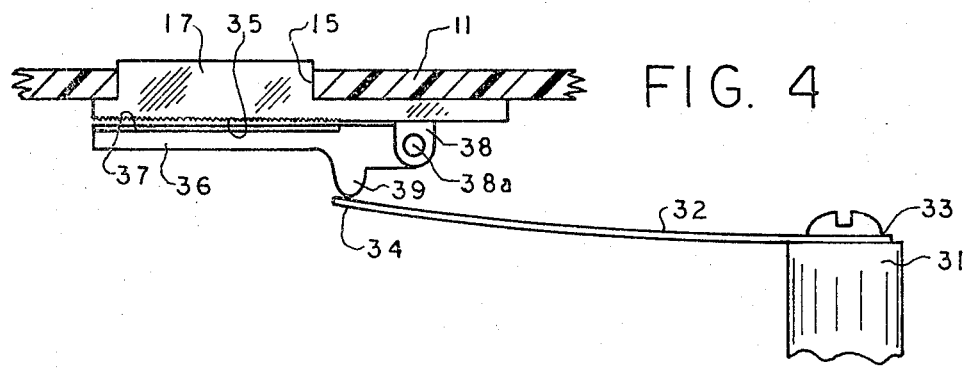
FIG. 4 is a partial cross-sectional side view similar to FIG. 3 showing the temperature indicator in a second operative position.
Figure 5:
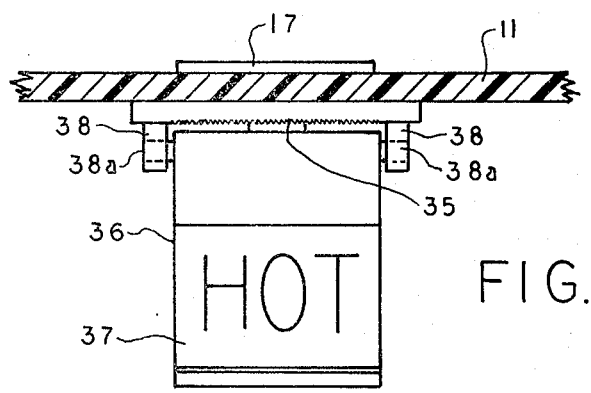
FIG. 5 is a partial cross-sectional view taken generally along lines 5—5 of FIG. 3.

As best seen in FIGS. 3-5, the arrangement 30 includes a temperature sensitive member 32 in the form of a bi-metallic strip which has one end 33 affixed to the upstanding post 31 and the other end 34 free to move between first and second vertical positions. In this regard, the end 34 moves upwardly as the temperature of the heating block 20 rises and vertically downwardly as the heating block cools.

The viewing window 17 is rendered partially opaque by frosting its under surface 35. Hingedly connected to the underside of the viewing window 17 is a movable member 36 which has a substantially planar upper surface 37 which includes a temperature indicia, such as for example, the word "HOT" as best seen in FIG. 5. The movable member 36 is hingedly connected to the underside of the viewing window 17 by a pivot arrangement comprising ears 38, 38 on the window 17 and pivot pins 38a, 38a on the member 36. The window 17 has a protuberance 39 with a rounded surface 40 that contacts the bi-metallic strip 32 at its free end 34. FIG. 3 illustrates the operative condition of the temperature indicating arrangement when the heating block and contact lens case are sufficiently cool to permit removal of the lens case 21 from the disinfector unit. Since the viewing window 17 is partially opaque and the movable member 36 is displaced from the under surface 35 of the viewing window 17, the temperature indicia word "HOT" carried on the planar surface 36 will not be discernable through the viewing window 17.

During the disinfecting cycle, as the heating block heats the lens case to a temperature considered to be excessively hot for removal of the lens case from the disinfector unit, the bi-metallic strip 32 will bend responsive to the temperature of the heating block so that the free end 34 will move upwardly. As the free end 34 moves upwardly, it actuates the temperature indicating arrangement by imparting pivotal movement to the movable member 36 until the planar surface 37 of movable member 36 is in surface contact with the under surface 35 of viewing window 17. The temperature indicia word "HOT" is then rendered viewable through the partially opaque window 17 to inform the user that the contact lens case is too hot for removal from the disinfector unit.

After the heating block 20 and lens case cool, the bi-metallic strip 32 will gradually return to its original condition as shown in FIG. 3 with its free end 34 moving downwardly so as to displace the planar surface 37 of the movable member 36 from the under surface 35 of the viewing window 17. Thus, when the contact lens case has cooled sufficiently, the movable member 36 will once again be in its position as shown in FIG. 3 for removing the temperature indicia word "HOT" from view through the partially opaque viewing window 17.

As a result, the user is now informed that the contact lens case has cooled sufficiently so as to enable removal of the contact lens case from the disinfector unit.

The invention is claimed as follows:

1. In a contact lens disinfector unit for the heat disinfecting of a pair of contact lenses contained within a lens case, wherein said unit includes a housing, a heating block within said housing arranged for contacting the lens case for heating the contact lenses in a contained solution to a disinfecting temperature; temperature indicating means for providing an indication as to the thermal status of the unit, said temperature indicating means comprising a viewing window carried by said housing and including an inner substantially planar surface, said window being partially opaque; a pivotally mounted indicator member having an upper, planar surface including temperature indicating indicia thereon, means pivotally mounting said indicator member for movement relative to said viewing window, such that said indicator member may be pivoted into position with the upper planar surface thereof in substantially flush contact with said substantially planar inner surface of the viewing window, said indicator member being pivotable away from said viewing window to move the planar surface thereof out of contact with the substantially inner planar surface of said window, with the temperature indicating indicia on said indicator member only being visible through said partially opaque viewing window when the respective surfaces thereof lie in substantially flush contact; and a bimetallic, elongate member having a first end associated with said heating block and a second end engaged with said indicator member, said second end being arranged to move in a first direction to cause said upper planar surface of the indicator member to move into flush contact with the inner surface of said viewing window, thereby rendering said indicia thereon visible through said window and to move into a second direction allowing said planar member to pivot away from said viewing window, thereby interrupting said flush contact and removing said indicia from view through said window.

2. A disinfector unit according to claim 1, wherein said viewing window is provided by a generally transparent member, with the inner planar surface thereof being frosted to render the resulting viewing window partially opaque.

3. A disinfector unit according to claim 1 or claim 2 wherein said viewing window is provided by a molded component fixed to the housing in association with an aperture formed therein, said component including a first portion providing said viewing window and a second portion to which said indicator is pivotally mounted.

4. A disinfector unit according to claim 1 or claim 2 wherein said temperature indicating means is mounted with respect to the housing, such that it is pivotable in a generally vertical plane, with movement of said indicator member away from said partially opaque viewing window being affected by gravity.

* * * * *